(12) United States Patent
Coghlan et al.

(10) Patent No.: US 6,514,991 B2
(45) Date of Patent: Feb. 4, 2003

(54) PHENYL-OXO-TETRAHYDROQUINOLIN-3-YL BETA-3 ADRENERGIC RECEPTOR AGONISTS

(75) Inventors: Richard Dale Coghlan, Freehold, NJ (US); William Floyd Fobare, Lawrenceville, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/904,116

(22) Filed: Jul. 12, 2001

(65) Prior Publication Data

US 2002/0068751 A1 Jun. 6, 2002

Related U.S. Application Data

(60) Provisional application No. 60/218,597, filed on Jul. 17, 2000.

(51) Int. Cl.[7] ............... A61K 31/4704; C07D 215/227
(52) U.S. Cl. ......................... 514/312; 546/153
(58) Field of Search ................ 546/153; 514/312

(56) References Cited

U.S. PATENT DOCUMENTS

| | | | |
|---|---|---|---|
| 5,561,142 A | * 10/1996 | Fisher et al. ............. | 514/312 |
| 5,578,620 A | 11/1996 | Fujita et al. | |
| 5,614,523 A | 3/1997 | Audia et al. | |
| 5,741,789 A | 4/1998 | Hibschman | |
| 5,786,356 A | 7/1998 | Bell et al. | |
| 5,789,402 A | 8/1998 | Audia et al. | |
| 6,069,176 A | * 5/2000 | Tsuchiya et al. ........... | 514/646 |

FOREIGN PATENT DOCUMENTS

| | | |
|---|---|---|
| EP | 0 449 261 A1 | 10/1991 |
| EP | 0 659 737 A2 | 6/1995 |
| EP | 0659737 * | 6/1995 |
| EP | 0 714 883 A1 | 6/1996 |
| EP | 0 764 640 A1 | 3/1997 |
| WO | WO 99/65895 | 12/1999 |
| WO | WO 01/17989 A2 | 3/2001 |
| WO | WO 01/44227 A1 | 6/2001 |

OTHER PUBLICATIONS

Marc S. Berridge et al., Nucl. Med. Biol., 1992, 563–569, 19(5).
Joan M Caroon et al., J. Pharm. Sci., Jan. 1987, 32–34, 76(1).
A. Guy et al., Synthesis, Sep. 1992, 821–22.
Manabu Hori et al., J. Org. Chem., 1998, 889–894, 63.
Yunsheng Huang et al., J. Med. Chem., 1998, 2361–2370, 41.
Bernard Hulin et al., J. Med. Chem., 1992, 1853–1864, 35.
Carl Kaiser et al., J. Med. Chem., 1977, 687–692, 20(5).
Yutaka Kawashima et al., Chem. Pharm. Bull, 1995, 1132–1136, 43(7).
Kiyoto Koguro et al., Synthesis, 1998, 910–914.
Gerard Leclerc et al., J. Med. Chem., 1980, 738–744, 23(7).
D. Mauleon et al., Il Farmaco,1989, 1109–1117, 44(11).
Alexander McKillop et al., J. Am. Chem. Soc., Sep. 1971, 4919–4920, 93(19).
Ricardo Tapia et al., Synthetic Communications, 1986, 681–687, 16(6).
Edward C. Taylor et al., Synthesis, Aug. 1981, 606–608.
Michiaki Tominaga et al., Chem. Pharm. Bull., 1987, 3699–3704, 35(9).
R.H. Uloth et al., J. Med. Chem., 1966, 88–97, 9.
Paul C. Unangst et al., J. Med. Chem., 1994, 322–328, 37.
Sophie VanWetswinkel et al., J. Anitbiotics, Sep. 1994, 1041–1051, 47(9).
S. Tamada et al., JP 01061468 A2 (English abstract), 1989.

* cited by examiner

Primary Examiner—Alan L. Rotman
Assistant Examiner—Rita Desai
(74) Attorney, Agent, or Firm—Kimberly R. Hild

(57) ABSTRACT

This invention provides compounds of Formula I having the structure

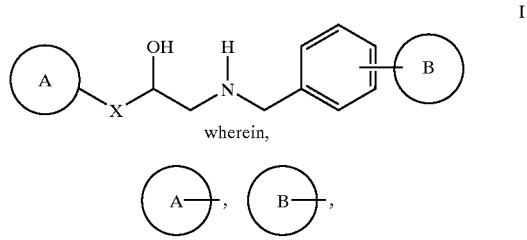

and X are as defined hereinbefore,
or a pharmaceutically acceptable salt thereof, which are useful in treating or inhibiting metabolic disorders related to insulin resistance or hyperglycemia (typically associated with obesity or glucose intolerance), atherosclerosis, gastrointestinal disorders, neurogenic inflammation, glaucoma, ocular hypertension and frequent urination; and are particularly useful in the treatment or inhibition of type II diabetes.

7 Claims, No Drawings

SEQUENCE LISTING

<160> NUMBER OF SEQ ID NOS: 8

<210> SEQ ID NO 1
<211> LENGTH: 25
<212> TYPE: DNA
<213> ORGANISM: Unknown
<220> FEATURE:
<223> OTHER INFORMATION: PCR primer, synthetic sequence

<400> SEQUENCE: 1
cttccctacc gccccacgcg cgatc                                         25

<210> SEQ ID NO 2
<211> LENGTH: 27
<212> TYPE: DNA
<213> ORGANISM: Unknown
<220> FEATURE:

-continued

<210> SEQ ID NO 2
<211> LENGTH: 27
<212> TYPE: DNA
<213> ORGANISM: Unknown
<220> FEATURE:
<223> OTHER INFORMATION: PCR primer, synthetic sequence

<400> SEQUENCE: 2
ctggcgccca acggccagtg gccagtc         27

<210> SEQ ID NO 3
<211> LENGTH: 27
<212> TYPE: DNA
<213> ORGANISM: Unknown
<220> FEATURE:
<223> OTHER INFORMATION: PCR primer, synthetic sequence

<400> SEQUENCE: 3
ttggcgctga tggccactgg ccgtttg         27

<210> SEQ ID NO 4
<211> LENGTH: 25
<212> TYPE: DNA
<213> ORGANISM: Unknown
<220> FEATURE:
<223> OTHER INFORMATION: PCR primer, synthetic sequence

<400> SEQUENCE: 4
gcgcgtagac gaagagcatc acgag           25

<210> SEQ ID NO 5
<211> LENGTH: 26
<212> TYPE: DNA
<213> ORGANISM: Unknown
<220> FEATURE:
<223> OTHER INFORMATION: PCR primer, synthetic sequence

<400> SEQUENCE: 5
ctcgtgatgc tcttcgtctc acgcgc          26

<210> SEQ ID NO 6
<211> LENGTH: 28
<212> TYPE: DNA
<213> ORGANISM: Unknown
<220> FEATURE:
<223> OTHER INFORMATION: PCR primer, synthetic sequence

<400> SEQUENCE: 6
gtgaaggtgc ccatgatgag acccaagg        28

<210> SEQ ID NO 7
<211> LENGTH: 27
<212> TYPE: DNA
<213> ORGANISM: Unknown
<220> FEATURE:
<223> OTHER INFORMATION: PCR primer, synthetic sequence

<400> SEQUENCE: 7
ccctgtgcac cttgggtctc atcatgg         27

<210> SEQ ID NO 8
<211> LENGTH: 22
<212> TYPE: DNA
<213> ORGANISM: Unknown
<220> FEATURE:
<223> OTHER INFORMATION: PCR primer, synthetic sequence

<400> SEQUENCE: 8
cctctgcccc ggttacctac cc              22

PHENYL-OXO-TETRAHYDROQUINOLIN-3-YL BETA-3 ADRENERGIC RECEPTOR AGONISTS

This application claims the benefit of U.S. Provisional Application No. 60/218,597, filed Jul. 17, 2000.

BACKGROUND OF THE INVENTION

This invention relates to phenyl-oxo-tetrahydroquinolin-3-yl β3 adrenergic receptor agonists useful for the treatment of metabolic disorders related to insulin resistance or hyperglycemia (typically associated with obesity or glucose intolerance), atherosclerosis, gastrointestinal disorders, neurogenic inflammation, glaucoma, ocular hypertension, frequent urination; and are particularly useful in the treatment or inhibition of type 11 diabetes.

The subdivision of β adrenergic receptors (β-AR) into $β_1$- and $β_2$-AR has led to the development of $β_1$- and $β_2$-antagonists and/or agonists which have been used in the treatment of cardiovascular disease and asthma. The recent discovery of "atypical" receptors, later called β-AR, has led to the development of $β_3$-AR agonists that are potentially useful as antiobesity and antidiabetic agents. For recent reviews on $β_3$-AR agonists, see: 1. Strosberg, A. D., *Annu. Rev. PharmacoL Toxicol.*, 1997, 37, 421; 2. Weber, A. E., *Ann. Rep. Med. Chem.*, 1998, 33, 193; 3. Kordik, C. P. and Reitz, A. B., *J. Med. Chem.*, 1999, 42, 181; 4. Weyer, C., Gautier, J. F., and Danforth, E., *Diabetes and Metabolism*, 1999, 25, 11.

Compounds that are potent and selective $β_3$ agonists, may be potentially useful antiobesity agents. Low levels or lack of $β_1$ and $β_2$-agonistic properties will minimize or eliminate the adverse side effects that are associated with $β_1$ and $β_2$ agonistic activities, i.e. increased heart rate, and muscle tremor, respectively. Early developments in the $β_3$-agonist field are described in European patent 427480, U.S. Pat. Nos. 4,396,627, 4,478,849, 4,999,377, and 5153210. These early patents purport to claim compounds with greater selectivity for the $β_3$-AR than for the $β_1$- and $β_2$-AR's. However, clinical trials in humans with such compounds have not been successful to date.

More recently, potent and selective human β3 agonists have been described in several patents and published applications: WO 98/32753, WO 97/46556, WO 97/37646, WO 97/15549, WO 97/25311, WO 96/16938, and WO 95/29159; European Patents 659737, 801060, 714883, 764640, and 827746; and U.S. Pat. Nos. 5,561,142, 5,705,515, 5,436,257, and 5,578,620. These compounds were evaluated in a Chinese hamster ovary (CHO) cell model, an assay that predicts the effects expected in humans. These assays utilize cloned human $β_3$ receptors, expressed in CHO cells (see refs. Granneman, et al., *Mol. Pharmacol.*, 1992, 42, 964; Emorine, et al., *Science*, 1989, 245, 1118; Liggett, *Mol. Pharmacol.*, 1992, 42, 634).

$β_3$-AR agonists also are useful in controlling urinary incontinence. It has been shown that relaxation of the bladder detrusor is under beta adrenergic control (Li, J. H., Yasay, G. D. and Kau, S. T., "Beta-adrenoceptor subtypes in the detrusor of guinea-pig urinary bladder", *Pharmacology*, 1992, 44, 13–18). Several laboratories have provided recent experimental evidence that activation of the $β_3$ receptor subtype by norepinephrine is responsible for relaxation of the urinary bladder in a number of animal species, including humans (Yamazaki Y., et al., "Species differences in the distribution of the β-AR subtypes in bladder smooth muscle", Br. *J. Pharmacol.*,1998, 124, 593–599).

Urge urinary incontinence is characterized by abnormal spontaneous bladder contractions that can be unrelated to bladder urine volume. Urge urinary incontinence is often referred to as hyperactive or unstable bladder. Several etiologies exist and fall into two major categories, myogenic and neurogenic. The myogenic bladder is usually associated with detrusor hypertrophy secondary to bladder outlet obstruction, or with chronic urinary tract infection. The neurogenic bladder is associated with an uninhibited micturition reflex, in which an upper motor neuron disease is usually the underlying cause. In either case, the disease is characterized by abnormal spontaneous contractions that result in an unusual sense of urinary urgency and involuntary urine loss. At present, the most common therapy for hyperactive bladder involves the use of antimuscarinic agents to block the action of the excitatory neurotransmitter acetylcholine. While effective in neurogenic bladders, their utility in myogenic bladders is questionable. In addition, due to severe dry mouth side-effects associated with antimuscarinic therapy, the patient compliance with these agents is only approximately 30 percent.

In the bladder, $β_3$-AR agonists activate adenylyl cyclase and generate cAMP through the G-protein coupled $β_3$-AR. The resulting phosphorylation of phospholamban/calcium ATPase enhances uptake of calcium into the sarcoplasmic reticulum, thereby decreasing intracellular calcium resulting in an inhibition of bladder smooth muscle contractility.

It is suggested therefore, that activation of the $β_3$-AR in the urinary bladder will inhibit abnormal spontaneous bladder contractions and be useful for the treatment of bladder hyperactivity. Note that unlike the antimuscarinics, $β_3$-AR agonists would be expected to be active against both neurogenic and myogenic etiologies.

Despite these recent developments there is still no single therapy available for the treatment of type II diabetes (NIDDM), obesity, atherosclerosis, gastrointestinal disorders, neurogenic inflammation, frequent urination and related diseases. A potent and selective $β_3$-AR agonist is therefore highly desirable for the potential treatment of these disease states.

DESCRIPTION OF THE INVENTION

This invention provides compounds of Formula I having the structure

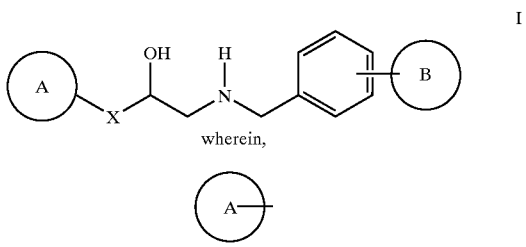

wherein, is (a) phenyl, optionally substituted with 1–3 Y groups;
(b) a 5- or 6-membered heterocyclic ring having 1–4 heteroatoms selected from O, N, and S, optionally substituted with 1–2 Y groups;
(c) a phenyl-fused heterocycle having 1–4 heteroatoms selected from O, N, and S, optionally substituted with 1–2 Y groups;
(d) a phenyl-fused heterocycle having 1–4 heteroatoms selected from O, N, and S, having a second phenyl ring fused to the heterocyclic ring, optionally substituted with 1–2 Y groups;

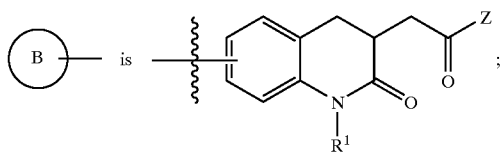

Y is hydroxy, halogen, cyano, —SO$_m$R$^2$, —SO$_n$R$^2$R$^3$, —NHSO$_2$R$^2$, —NR$^2$R$^3$, alkyl of 1–10 carbon atoms, cycloalkyl of 3–8 carbon atoms, alkoxy of 1–10 carbon atoms, arylalkoxy, —COR$^2$, or —CO$_2$R$^2$;
X is —OCH$_2$— or a bond;
Z is —OR$^2$ or —NR$^2$R$^3$;
R$^1$ is hydrogen, alkyl of 1–6 carbon atoms, or cycloalkyl of 3–8 carbon atoms;
R$^2$ and R$^3$ are each, independently, hydrogen; alkyl of 1–10 carbon atoms which may be optionally substituted with 1–5 substituents selected from the group consisting of halogen, hydroxy, phenyl optionally substituted with 1–2 W groups, oxo, —CO$_2$R$^4$, —NR$^4$R$^5$, and —NHCOR$^4$; cycloalkyl of 3–8 carbon atoms; arylalkyl having 1–10 carbon atoms in the alkyl moiety; or heterocycle or heterocycle-alkyl, where the alkyl moiety has 1–5 carbon atoms and the heterocycle is:
  (a) a 5- or 6-membered heterocyclic ring having 1–4 heteroatoms selected from O, N, and S, optionally substituted with 1–2 Y groups;
  (b) a phenyl-fused heterocycle having 1–4 heteroatoms selected from O, N, and S, optionally substituted with 1–2 Y groups;
  (c) a phenyl-fused heterocycle having 1–4 heteroatoms selected from O, N, and S, having a second phenyl ring fused to the heterocyclic ring, optionally substituted with 1–2 Y groups;
R$^4$ and R$^5$ are each, independently, hydrogen, alkyl of 1–10 carbon atoms, or cycloalkyl of 3–8 carbon atoms;
W is hydroxy, halogen, alkyl of 1–10 carbon atoms, arylalkoxy having 1–6 carbon atoms in the alkyl moiety, —NHC(O)NHR$^4$, NR$^4$R$^5$, —OR$^4$, —COR$^4$, —CO$_2$R$^4$, —SO$_m$R$^4$, —SO$_n$R$^4$R$^5$;
m=0–2;
n=1–2;
or a pharmaceutically acceptable salt thereof, which are selective agonists at human β$_3$ adrenergic receptors and are useful in treating or inhibiting metabolic disorders related to insulin resistance or hyperglycemia (typically associated with obesity or glucose intolerance), atherosclerosis, gastrointestinal disorders, neurogenic inflammation, glaucoma, ocular hypertension, and frequent urination; and are particularly useful in the treatment or inhibition of type II diabetes.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, such as alkali metal salts (for example, sodium, lithium, or potassium) alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group, when a compound of this invention contains an acidic moiety.

The compounds of the instant invention all contain at least one asymmetric center. Additional asymmetric centers may be present in the molecule depending upon the nature of the various substituents in the molecule. Each such asymmetric center will produce two optical isomers and all such optical isomers, as separated, pure or partially purified optical isomers or racemic mixtures thereof, are included within the scope of the instant invention. Any enantiomer of a compound of the general Formula I may be obtained by stereospecific synthesis using optically pure starting materials of known configuration.

Alkyl and alkenyl include both straight chain as well as branched moieties. Halogen means bromine, chlorine, fluorine, and iodine. Aryl includes monocyclic or bicyclic aromatic carbocyclic groups such as phenyl and naphthyl. Benzyl is the preferred arylalkyl moiety.

As used herein, a heterocyclic ring is a ring containing 1–4 heteroatoms selected from N, O, and S, and includes a heterocycle that may be saturated, unsaturated, or partially unsaturated. The heterocyclic ring may be attached within structural Formula I by any carbon atom or appropriate heteroatom. It is understood that the heterocyclic ring does not contain heteroatoms in arrangements that would make them inherently unstable. For example, the term heterocyclic ring does not include ring systems containing O—O bonds in the ring backbone. Preferred 5- and 6-membered heterocycles include pyridinyl, thiophenyl, furanyl, thiadiazolyl, thiazolyl, oxadiazolyl, carbazolyl, pyrrolyl, imidazolyl and pyrazolyl. Preferred phenyl-fused heterocycles include benzothiophenyl, benzofuranyl, benzodioxolyl, quinolinyl, benzimidazolyl, benzotriazolyl, 1,2,3,4-tetrahydroquinolyl, and 1,2,3,4-tetrahydroisoquinolyl.

Preferred compounds of Formula I are those in which

is
a phenyl ring, optionally substituted with 1–3 Y groups;
X is a bond;
Z is OR$^2$;
R$^1$ is hydrogen;
or a pharmaceutically acceptable salt thereof, with the remaining substituents as defined above.

Specifically preferred compounds of this invention are:
a) [7-(4-{[(2R)-2-Hydroxy-2-(4-hydroxy-3-methanesulfonylamino-phenyl)-ethylamino]-methyl}- phenyl)-2-oxo-1,2,3,4-tetrahydro-quinolin-3-yl]-acetic acid methyl ester;

b) [7-(3-{[(2R)-2-Hydroxy-2-(4-hydroxy-3-methanesulfonylamino-phenyl)-ethylamino]-methyl}-phenyl)-2-oxo-1,2,3,4-tetrahydro-quinolin-3-yl]-acetic acid methyl ester;

c) Ethyl [6-(4-{[((2R)-2-hydroxy-2-{4-hydroxy-3-[(methylsulfonyl)amino]-phenyl}ethyl)amino]methyl}phenyl)-2-oxo-1,2,3,4-tetrahydroquinolin-3-yl] acetate;

d) Ethyl [6-(3-{[((2R)-2-hydroxy-2-{4-hydroxy-3-[(methylsulfonyl)amino]-phenyl}ethyl)amino]methyl}phenyl)-2-oxo-1,2,3,4-tetrahydroquinolin-3-yl] acetate; or a pharmaceutically acceptable salt thereof.

The compounds of this invention were prepared according to the following schemes from commercially available starting materials or from starting materials that were prepared by methods commonly known to those skilled in the art. The 2-chloroquinoline 1 was refluxed in aqueous acid-methanol to yield the oxo species 2. Catalytic hydrogenation of the double bond with a suitable catalyst and demethylation of the methyl ether yielded the 7-hydroxy-2-oxo-tetrahydroquinoline 4. Triflate formation with triflic anhydride and palladium catalyzed coupling with an aryl boronic acid yielded the corresponding aldehyde 6. Reductive amination of the aldehyde 6 with the amine 8 using sodium cyanoborohydride in alcohol yielded the desired product 7 of formula I.

using literature procedures. These schemes show the preparation of representative compounds of this invention.

In Scheme 1 the 2-chloro-7-methoxy-quinoline-3-acetic acid methyl ester 1 is known in the literature (*J. Chem. Soc. Perkins* 1, 1981, 1537–1543) or readily prepared

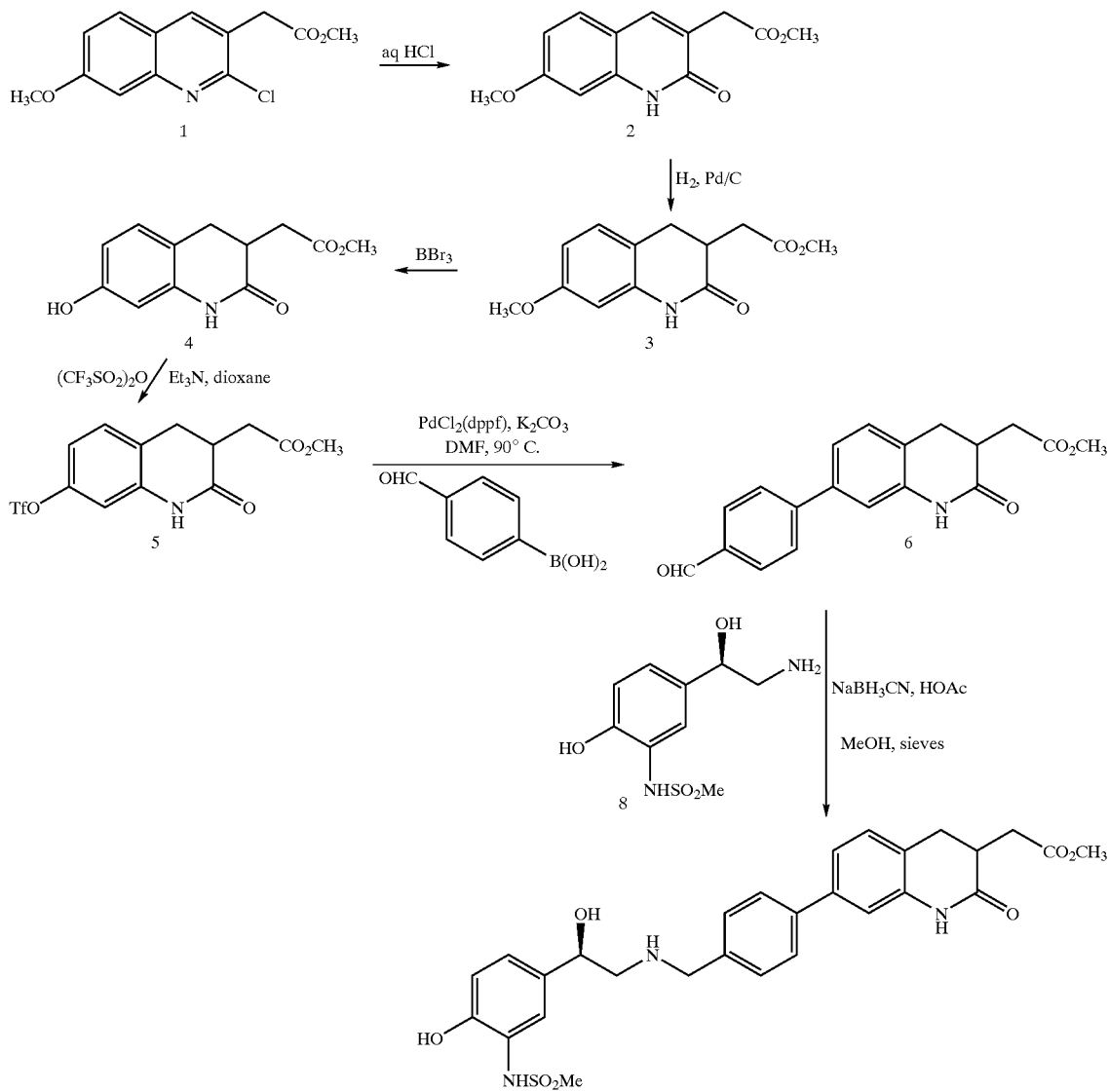

SCHEME 1

The synthesis of the 6-substituted tetrahydroquinolines began with the commercially available 5-hydroxy-2-nitrobenzaldehyde. Condensation with

SCHEME 2

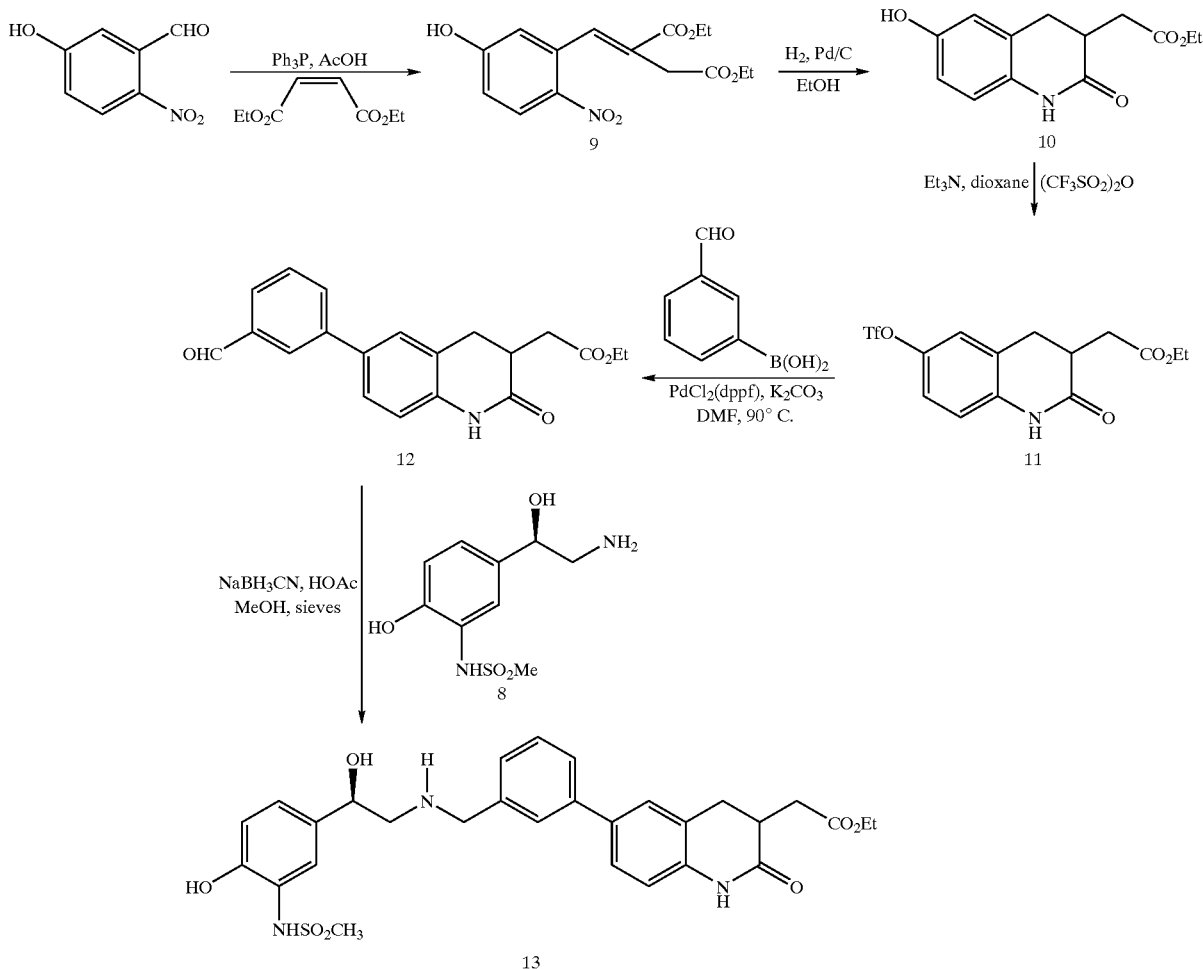

triphenylphosphine and diethyl maleate gave adduct 9 (Scheme 2). Catalytic hydrogenation of the nitro group and the olefin yielded the substituted quinolinone 10. Triflate formation with triflic anhydride and palladium catalyzed coupling with an aryl boronic acid yielded the corresponding aldehyde 11. Reductive amination of the aldehyde 11 with the amine 8 using sodium cyanoborohydride in alcohol yielded the desired product 12 of formula I.

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of the compounds of this invention to treat or inhibit disorders related to insulin resistance or hyperglycemia was confirmed with representative compounds of this invention in the following standard pharmacological test procedures, which measured the binding selectivity of the $\beta_1$-, $\beta_2$-, and $\beta_3$-AR. Binding to the receptors was measured in Chinese Hamster ovary (CHO) cells that were transfected with $\beta_1$-, $\beta_2$-, and $\beta_3$-AR's. The following briefly summarizes the procedures used and results obtained.

Transfection of CHO cells with $\beta_1$- and $\beta_2$-AR:

CHO cells were transfected with human $\beta_1$- or $\beta_2$-AR as described in Tate, K M., Eur. *J Biochem.*, 1991, 196, 357–361.

Cloning of Human $\beta_3$-AR Genomic DNA:

cDNA was constructed by ligating four polymerase chain reaction (PCR) products using the following primers: an ATG-NarI fragment, sense primer 5'-CTTCCCTACCGCCCCACGCGCGATC3' and anti-sense primer 5' CTGGCGCCCAACGGCCAGTGGC-CAGTC3'; a NarI-AccI fragment, 5'TTGGCGCTGATGGC-CACTGGCCGTTTG3' as sense and 5'GCGCGTAGACGAAGAGCATCACGAG3' as anti-sense primer; an AccI-StyI fragment, sense primer 5° CTCGT-GATGCTCTTCGTCTCACGCGC3' and anti-sense primer 5'GTGAAGGTGCCCATGATGAGACCCAAGG3' and a StyI-TAG fragment, with sense primer 5° CCCTGTGCAC-CTTGGGTCTCATCATGG3' and anti-sense primer 5° CCTCTGCCCCGGTTACCTACCC3'. The corresponding primer sequences are described in Mantzoros, C. S., et.al., *Diabetes,* 1996, 45, 909–914. The four fragments are ligated into a pUC 18 plasmid (Gibco-BRL) and sequenced. Full-length $\beta_3$-AR clones (402 amino acids) containing the last 6 amino acids of h$\beta_3$-AR are prepared with the $\beta_3$-$\beta$ARpcDNA3 from ATTC.

Binding Procedure:

Clones expressing receptor levels of 70 to 110 fmoles/mg protein were used in the test procedures. CHO cells were grown in 24-well tissue culture plates in Dulbecco's Modified Eagle Media with 10% fetal bovine serum, MEM non-essential amino acids, Penicillin-Streptomycin and Geneticin. On the day of test procedure, growth medium was replaced with preincubation media (Dulbecco's Modified Eagle Media) and incubated for 30 minutes at 37° C. Pre-incubation medium was replaced with 0.2 ml treatment medium containing DMEM media containing 250 $\mu$M IBMX (isobutyl-1-methylxantine) plus 1 mM ascorbic acid with test compound dissolved in DMSO. Test compounds were assayed over a concentration range of $10^{-9}$ M to $10^{-5}$M for $\beta_3$-AR transfected cells and $10^{-8}$ to $10^{-4}$ M for $\beta_3$-AR and $\beta_2$-AR transfected cells. Isoproterenol ($10^{-5}$ M) was used as an internal standard for comparison of activity. Cells were incubated at 37° C. on a rocker for 30 min with the $\beta_3$-AR transfected cells and 15 min with $\beta_1$-AR and $\beta_2$-AR transfected cells. Incubation was stopped by the addition of 0.2N HCl and the acid was neutralized with 2.5N NaOH. The plates, containing the cells and neutralized media, were stored at −20° C. until ready to test for cAMP using the SPA test kit (Amersham).

Data Analysis and Results:

Data collected from the SPA test procedure were analyzed as percent of the maximal isoproterenol response at $10^{-5}$ M. Activity curves were plotted using the SAS statistical and graphics software. $EC_{50}$ values were generated for each compound and the maximal response (IA) exhibited by each compound was compared to the maximal response of isoproternol at $10^{-5}$ M from the following formula:

$$IA = \frac{\% \text{ activity compound}}{\% \text{ activity isoproterenol}}$$

Shown in Table I are the $\beta_3$-AR $EC_{50}$ and IA values for the representative compounds of this invention that were evaluated in this standard pharmacological test procedure. Compounds of the present invention were active at the $\beta_3$-AR as shown by these results. The compounds of this invention were considerably less active, if at all, at the $\beta_1$- and/or $\beta_2$-AR.

TABLE I

| Compound No. | $EC_{50}(\beta3)$, nM | $IA(\beta3)$ |
|---|---|---|
| Example 1 | 40.0 | 1.1 |
| Example 2 | 90.0 | 1.0 |
| Example 3 | 60.0 | 1.0 |
| Example 4 | 70.0 | 1.0 |

Based on these results, representative compounds of this invention have been shown to be selective $\beta_3$-AR agonists. They are therefore useful in treating metabolic disorders related to insulin resistance or hyperglycemia (typically associated with obesity or glucose intolerance), atherosclerosis, gastrointestinal disorders, neurogenic inflammation, glaucoma, ocular hypertension, and frequent urination; and are particularly useful in the treatment or inhibition of type II diabetes, and in modulating glucose levels in disorders such as type I diabetes. As used herein, the term modulating means maintaining glucose levels within clinically normal ranges.

As used in accordance with this invention, the term providing an effective amount means either directly administering such a compound of this invention, or administering a prodrug, derivative, or analog which will form an effective amount of the compound of this invention within the body.

It is understood that the effective dosage of the active compounds of this invention may vary depending upon the particular compound utilized, the mode of administration, and severity of the condition being treated, as well as the various physical factors related to the individual being treated. As used in accordance with this invention, satisfactory results may be obtained when the compounds herein are administered at a daily dosage of 0.1 mg to 1 mg per kilogram of body weight, preferably in divided doses two to six times per day, or in a sustained release form. For most large mammals, the total daily dosage is from 3.5 mg to 140 mg. It is preferred that the administration of one or more of the compounds herein begin at a low dose and be increased until the desired effects are achieved.

Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidinone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s).

In some cases it may be desirable to administer the compounds directly to the airways in the form of an aerosol.

The compounds of this invention may also be administered parenterally or intraperitoneally. Solutions or suspensions of these active compounds as free bases or pharmacologically acceptable salts can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for administration by syringe include sterile aqueous solutions or dispersions and sterile powders for the extemporaneous preparation of sterile injectable solutions or dispersions. The form must be sufficiently fluid to permit administration by syringe. It must be stable under the conditions of manufacture and storage and must be preserved against the contaminating action of microorganisms. The carrier can be a solvent or dispersion medium containing, for example, water, ethanol, polyol (e.g., glycerol, propylene glycol and liquid polyethylene glycol), suitable mixtures thereof, and vegetable oils.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The compounds of the present invention also possess utility for increasing lean meat deposition and/or improving lean meat to fat ratio in edible animals, i.e. ungulate animals and poultry.

Animal feed compositions effective for increasing lean meat deposition and for improving lean meat to fat ratio in poultry, swine, sheep, goats, and cattle are generally prepared by mixing the compounds herein with a sufficient amount of animal feed to provide from 1 to 1000 ppm of the compound in the feed. Animal feed supplements can be prepared by admixing 75% to 95% by weight of a compound of this invention with 5% to 25% by weight of a suitable carrier or diluent. Carriers suitable for use to make up the feed supplement compositions include the following: alfalfa meal, soybean meal, cottonseed oil meal, linseed oil meal, sodium chloride, cornmeal, cane molasses, urea, bone meal, corncob meal and the like. The carrier promotes a uniform distribution of the active ingredients in the finished feed into which the supplement is blended. It thus performs an important function by ensuring proper distribution of the active ingredient throughout the feed. When the supplement is used as a top dressing for the feed, the carrier likewise helps to ensure a uniform distribution of the active compound across the top of the dressed feed.

The preferred medicated swine, cattle, sheep and goat feed generally contain from 0.01 to 400 grams of active ingredient per ton of feed, the optimum amount for these animals usually being 50 to 300 grams per ton of feed. The preferred poultry and domestic pet feed usually contain 0.01 to 400 grams and preferably 10 to 400 grams of active ingredient per ton of feed.

For parenteral administration, the compounds described herein may be prepared in the form of a paste or a pellet and administered as an implant, usually under the skin of the head or ear of the animal in which an increase in lean meat deposition and/or an improvement in lean meat to fat ratio is sought. Parenteral administration involves injection of a sufficient amount of the compounds of the present invention to provide the animal with 0.001 to 100 mg/kg/day of body weight of the active ingredient. The preferred dosage for swine, cattle, sheep and goats is in the range of 0.001 to 50 mg/kg/day of body weight of active ingredient. The preferred dosage for poultry and domestic pets is usually in the range of 0.001 to 35 mg/kg/day of body weight.

Paste formulations can be prepared by dispersing the active compounds in pharmaceutically acceptable oils such as peanut oil, sesame oil, corn oil or the like. Pellets containing an effective amount of the compounds herein can be prepared by admixing these compounds with a diluent such as carbowax, carnuba wax, and the like, and a lubricant, such as magnesium or calcium stearate, can be added to improve the pelletizing process. It is recognized that more than one pellet may be administered to an animal to achieve the necessary dosage that will provide the desired increase in lean meat deposition and/or improvement in lean meat to fat ratio. Moreover, it has been found that implants may also be employed periodically during the animal treatment period in order to maintain the proper drug level in the animal's body. For poultry and swine farmers, the method of this invention results in leaner animals.

The compounds of this invention are also useful in elevating the lean mass to fat ratio in domestic pets. For the pet owner or veterinarian who wishes to increase leanness and trim unwanted fat from pets, the present invention provides the means by which this can be accomplished.

The preparation of representative examples of this invention is described below.

EXAMPLE 1

[7-(4-{[(2R)-2-Hydroxy-2-(4-hydroxy-3-methanesulfonylamino-phenyl)-ethylamino]-methyl}-phenyl)-2-oxo-1,2,3,4-tetrahydro-quinolin-3-yl]-acetic Acid Methyl Ester Step A A suspension of compound 1 (12.1 g, 46.0 mmol) in methanol (175 mL) was treated with 12 N aq HCl and heated to reflux forming a solution. After 21 h, the resulting precipitate was cooled to 0° C. for 1 h. Vacuum filtration gave compound 2 (11.0 g, 96% yield) as a yellow crystalline solid. Mp 195.0-96.5° C. $^1$H NMR (DMSO-$d_6$, 300 MHz): δ 3.49 (s, 2H, C$\underline{H}_2$), 3.59 (s, 3H, CO$_2$C$\underline{H}_3$), 3.79 (s, 3H, OC$\underline{H}_3$), 6.77–6.81 (overlapping m, 2H, Ar$\underline{H}$), 7.53 (d, J=9 Hz, 1H, Ar$\underline{H}$), 7.76 (s, 1H, ArC$\underline{H}$=), 11.7 (s, 1H, ArN$\underline{H}$).

Step B

A suspension of compound 2 (9.0 g, 36 mmol) in acetic acid (900 mL) was hydrogenated over 10% Pd-C (9.0 g) at 50 psi. After 6 days, the catalyst was filtered (Celite) and washed with acetic acid (2×500 mL). Concentration of the filtrate gave a tan crystalline solid (9.5 g). Recrystallization from hot ethanol (100 mL) gave compound 3 (5.7 g, 63% yield) as white needles. Mp 153-55° C. $^1$H NMR (DMSO-d6, 300 MHz): δ 2.44 (m, 1H, ArC$\underline{H}$H), 2.68–2.87 (overlapping m, 4H, ArCH$\underline{H}$, CH, C$\underline{HH}$HCO$_2$), 3.59 (s, 3H, CO$_2$C$\underline{H}_3$), 3.68 (s, 3H, OC$\underline{H}_3$), 6.44 (d, J=2.5 Hz, 1H, Ar$\underline{H}$), 6.49 (dd, J=2.5 Hz, 8 Hz, 1H, Ar$\underline{H}$), 7.05 (d, J=8 Hz, 1H, Ar$\underline{H}$), 10.1 25 (s,1H, ArN$\underline{H}$).

Step C

A solution of compound 3 (10.4 g, 41.7 mmol) in methylene chloride (100 mL) was treated with 1.0 M BBr$_3$—CH$_2$Cl$_2$ solution (410 mL, 410 mmol) at 0° C. in an oven-dried flask. After 3 h, the resulting mixture was concentrated at reduced pressure and the residue was treated with ice-cold methanol (800 mL) and concentrated. Methanol treatment and concentration were repeated twice more to give a tan foam. Flash column chromatography on silica gel eluting with 2.5% NH$_3$-saturated MeOH/CHCl$_3$ gave compound 4 (5.5 g, 56% yield) as a pale yellow solid. Mp 177-80° C. $^1$H NMR (DMSO-$d_6$, 300 MHz): δ 2.43 (m, 1H, ArC$\underline{H}$H), 2.59–2.81 (overlapping m, 4H, ArCH$\underline{H}$, C$\underline{H}$, C$\underline{HH}$CO$_2$), 3.59 (s, 3H, C$\underline{H}_3$), 6.28–6.33 (overlapping m, 2H, Ar$\underline{H}$), 6.90 (d, J=8 Hz, 1H, Ar$\underline{H}$), 9.27 (s, 1H, ArO$\underline{H}$), 10.0 (s, 1H, ArN$\underline{H}$).

Step D

To a suspension of compound 4 (2.1 g, 8.9 mmol) and triethylamine (6.3 mL, 45 mmol) in 1,4-Dioxane (ca. 100 mL) at 0° C. under nitrogen was added triflic anhydride (3.0 mL, 18 mmol) dropwise via syringe during 5–10 min. After the addition was complete the mixture was warmed to room temperature. After 3 days, the resulting solution was concentrated at reduced pressure and the dark oil was taken up in methylene chloride (300 mL), washed with water, 5% aq NaHCO$_3$ and brine (150 mL each), dried (MgSO$_4$) and concentrated at reduced pressure to give a mixture of oil and solid. Flash column chromatography on silica gel (85 g) eluting with ethyl acetate-hexanes (gradient elution: 10, 20, then 40%) gave compound 5 (2.3g, 70% yield) as a pale yellow crystalline solid after recrystallization from ethyl acetate-hexanes. Mp 141-42° C. IR (KBr): 1725 (s), 1690 (s) cm$^{-1}$. $^1$H NMR (DMSO-d$_6$, 400 MHz): δ 2.49–2.53 (m, 1H, ArCHH), 2.73–3.01 (overlapping m, 4H, ArCH<u>H</u>, C<u>H</u>, C<u>HH</u>CO$_2$), 3.60 (s, 3H, C<u>H</u>$_3$), 6.90 (d, J=3 Hz, 1H, Ar<u>H</u>), 7.01 (m, 1H, Ar<u>H</u>), 7.35 (d, J=8 Hz, 1H, Ar<u>H</u>), 10.4 (s, 1H, N<u>H</u>). MS (pos. APCI) m/e (rel. intensity): 368 (M+H, 100). Analysis calc. for C$_{13}$H$_{12}$F$_3$NO$_6$S: C, 42.51;H, 3.29; N, 3.81. Found: C, 42.59;H, 3.30; N, 3.82.

Step E

Compound 5 (1.25 g, 3.4 mmol), 4-formylphenylboronic acid (0.56 g, 3.7 mmol), [1,1'-Bis(diphenylphosphino) ferrocene]dichloropalladium(II).CH$_2$Cl$_2$ (0.14 g, 0.17 mmol), and potassium carbonate (1.2 g, 8.5 mmol) were combined in de-gassed N,N-Dimethyl formamide (20 mL) at room temperature under nitrogen in a flame-dried flask. The mixture was heated at 90° C. (oil bath) for 24 hours at which time additional catalyst was added and heating was continued for an additional 24 hours. The cooled mixture was poured into water (170 mL) and extracted with ethyl acetate (3×170 mL). The combined extracts were washed with 0.1 N aq NaOH (170 mL) and brine (3×170 mL), dried (K$_2$CO$_3$) and concentrated at reduced pressure to give a dark brown solid (1.1 g). Flash column chromatography on silica gel (70 g) eluting chloroform followed by 0.5% NH$_3$- saturated MeOH/CHCl$_3$ yielded compound 6 (0.85 g, 77% yield) as a pale yellow solid. IR (KBr): 1740 (s), 1699 (s), 1675 (s) cm$^{-1}$. $^1$H NMR (DMSO-d$_6$, 400 MHz): δ 2.49–2.54 (m, 1H, ArCH<u>H</u>), 2.76–3.00 (overlapping m, 4H, ArCH<u>H</u>, C<u>H</u>, CH<u>H</u>CO$_2$), 3.62 (s, 3H, C<u>H</u>$_3$), 7.20 (s, 1H, Ar<u>H</u>), 7.30 (s, 2H, Ar<u>H</u>), 7.79 (d, J=8 Hz, 2H, Ar<u>H</u>), 7.99 (d, J=8 Hz, 2H, Ar<u>H</u>), 10.0 (s, 1H, C<u>H</u>O), 10.3 (s, 1H, N<u>H</u>). MS (pos. APCl) m/e (rel. intensity): 322 (M−H, 100). Analysis calc. for C$_{19}$H$_{17}$NO$_4$: C, 70.58;H, 5.30; N, 4.33. Found: C, 70.39;H, 5.31; N, 4.31.

Step F

Compound 6 (324 mg, 1.0 mmol), compound 8 (247 mg, 1.0 mmol) and 3 Å molecular sieves were combined in methanol (10 mL) at room temperature under nitrogen in a flame-dried flask. Acetic acid (0.12 mL, 2.1 mmol) was added and the mixture was stirred overnight. After 20 hours sodium cyanoborohydride (87 mg, 1.3 mmol) was added and the suspension was stirred for an additional 22 hours, at which time the mixture was vacuum filtered (Celite), washed with methanol and concentrated under reduced pressure. The resulting pale yellow foam was treated with NH$_3$-saturated methanol (20 mL) and concentrated under reduced pressure. This treatment was repeated to yield a tan foam. Flash column chromatography on silica gel (30 g) eluting NH$_3$-saturated MeOH/CHCl$_3$ (gradient elution: 2.5, 5, then 10%) gave the title compound, 7, (224 mg, 40% yield) as a pale yellow foam. IR (KBr): 3275 (broad, m), 1730 (m), 1670 (s) cm$^{-1}$. $^1$H NMR (DMSO-d$_6$, 400 MHz): δ 2.48–2.53 (m, 1H, ArCH<u>H</u>), 2.60 (overlapping m, 2H, CHC<u>HH</u>N), 2.75–2.97 (overlapping s, m, 7H, ArCH<u>H</u>, C<u>H</u>CONH, C<u>HH</u>CO$_2$, SO$_2$C<u>H</u>$_3$), 3.61 (s, 3H, OC<u>H</u>$_3$), 3.75 (m, 2H, ArC<u>HH</u>N), 4.55 (m, 1H, ArC<u>H</u>OH), 5.20 (broad s, 1H), 6.80 (d, J=8 Hz, 1H, Ar<u>H</u>), 6.98 (m, 1H, Ar<u>H</u>), 7.11 (d, J=2 Hz, 1H, Ar<u>H</u>), 7.17–7.24 (overlapping m, 3H, Ar<u>H</u>), 7.38 (d, J=8 Hz, 2H, Ar<u>H</u>), 7.49 (d, J=8 Hz, 2H, Ar<u>H</u>), 9.00 (broad s, 1H, ArN<u>H</u>SO2), 10.2 (s,1H, ArN<u>H</u>CO). MS (pos. ESI) m/e (rel. intensity): 554 (M+H, 100).

EXAMPLE 2

Ethyl [6-(3-{[((2R)-2-hydroxy-2-[4-hydroxy-3-[(methylsulfonyl)amino]phenyl ethyl)amino] methyl}phenyl)-2-oxo-1,2,3,4-tetrahydroquinolin-3-yl] acetate Step A Triphenylphosphine (12.2 g, 46.5 mmol) and diethyl maleate (8.0 g, 46.5 mmol) were combined in glacial acetic acid (70 mL) at room temperature and the slurry stirred for 6.5 h at which time the resulting solution was treated with 5-hydroxy-2-nitrobenzaldehyde (5.2 g, 31 mmol). Benzene (250 mL) was added and the solution heated to reflux. After 18 h, the solution was concentrated at reduced pressure to give a clear orange oil (27.6 g). Flash column chromatography on silica gel (700 g) eluting with ethyl acetate-hexanes (gradient elution: 5, 10, 20, then 40%) gave compound 9 (6.9 g; 69% yield) as a pale yellow solid. $^1$H NMR: (DMSO-d$_6$, 300 MHz): δ 1.15 (t, J=7.5 Hz, 3H, C<u>H</u>$_3$), 1.22 (t, J=7.5 Hz, 3H, C<u>H</u>$_3$), 3.25 (s, 2H, C<u>H</u>$_2$CO$_2$), 4.05 (q, J=7.5 Hz, 2H, CO$_2$C<u>H</u>$_2$), 4.20 (q, J=7.5 Hz, 2H, CO$_2$C<u>H</u>$_2$), 6.70 (s, 1H, Ar <u>H</u>), 6.95 (d, J=9 Hz, 1H, Ar<u>H</u>), 7.99 (s, 1H, C<u>H</u>=), 8.13 (d, J=9 Hz, 1H, Ar<u>H</u>), 11.2 (s, 1H, ArO<u>H</u>).

Step B

A solution of compound 9 (3.8 g, 12 mmol) in ethanol (35 mL) was hydrogenated over 10% Pd-C (0.8 g) at room temperature and 1 atm. After 20 h, the catalyst was filtered (Celite) and washed with ethanol (3×35 mL). Concentration of the filtrate gave a mixture of solid and foam (2.8 g). Flash column chromatography on silica gel (190 g) eluting with ethyl acetate-hexanes (gradient elution: 20, then 40%) gave compound 10 (1.3 g, 45% yield) as a pale yellow solid. $^1$H NMR: (DMSO-d$_6$, 300 MHz): δ 1.18 (t, J=7.5 Hz, 3H, C<u>H</u>$_3$), 2.15–2.80 (overlapping m, 5H, ArC<u>HH</u>, CHC<u>HH</u>), 4.05 (q, J=7.5 Hz, 2H, CO$_2$C<u>H</u>$_2$), 6.53 (overlapping s, d, 2H, Ar<u>H</u>), 6.66 (d, J=9 Hz, 1H, Ar<u>H</u>), 9.03 (s, 1H, ArO<u>H</u>), 9.95 (s, 1H, ArN<u>H</u>).

Step C

To a suspension of compound 10, (2.7 g, 11 mmol) and triethylamine (7.5 mL, 54 mmol) in 1,4-dioxane (100 mL) at 0° C. under nitrogen was added triflic anhydride (3.6 mL, 21 mmol) dropwise via syringe over a 5–10 minutes. After the addition was complete the mixture was warmed to room temperature. After 3 days, the resulting solution was concentrated at reduced pressure and the dark oil was dissolved in methylene chloride (300 mL), washed with water, 5% aq NaHCO$_3$ and brine (150 mL each), dried (MgSO4) and concentrated at reduced pressure to give a mixture of oil and solid (5.1 g). Flash column chromatography on silica gel (85 g) eluting with ethyl acetate-hexanes (gradient elution: 10, 20, then 40%) gave compound 11 (3.2 g, 78% yield) as pale yellow needles after recrystallization from hot ethyl acetate-hexanes. Mp 108-09° C. IR (KBr): 1730 (s), 1680 (s) cm$^{-1}$. $^1$H NMR (DMSO-d$_6$, 400 MHz): δ 1.19 (t, J=7 Hz, 3H, C<u>H</u>$_3$), 2.47 (m, 1H, ArCH<u>H</u>), 2.75 (dd, J=5 Hz, 16 Hz, 1H, ArCH<u>H</u>), 2.87 (m, 2H, C<u>HH</u>CO$_2$), 3.01 (m, 1H, C<u>H</u>), 4.07 (q, J=7 Hz, 2H, C<u>H</u>$_2$), 6.96 (d, J=9 Hz, 1H, Ar<u>H</u>), 7.28 (m, 1H, Ar<u>H</u>), 7.36 (d, J=3 Hz, 1H, Ar<u>H</u>), 10.4 (s, 1H, N<u>H</u>). MS (pos. APCI) m/e (rel. intensity): 380 (M−H, 18). Analysis calc. for C$_{14}$H$_{14}$F$_3$NO$_6$S: C, 44.10;H, 3.70; N, 3.67. Found: C, 43.98;H, 3.82; N, 3.59.

Step D

Compound 11 (1.5 g, 3.9 mmol), 3-formylphenylboronic acid (0.68 g, 4.3 mmol), [1,1'-bis(diphenylphosphino) ferrocene]dichloropalladium(II).CH$_2$Cl$_2$ (0.16 g, 0.20 mmol), and potassium carbonate (1.4 g, 10 mmol) were combined in de-gassed N,N-Dimethyl formamide (20 mL) at room temperature under nitrogen in a flame-dried flask. The mixture was heated at 90° C. (oil bath) for 24 hours at which time additional catalyst was added and heating was continued for an additional 24 hours. The cooled mixture was poured into water (170 mL) and extracted with ethyl acetate (3×170 mL). The combined extracts were washed with 0.1 N aq NaOH (170 mL) and brine (3×170 mL), dried ($K_2CO_3$) and concentrated under reduced pressure to give a dark brown solid (1.2 g). Flash column chromatography on silica gel (70 g) eluting chloroform followed by 0.5% $NH_3$-saturated $MeOH/CHCl_3$ gave compound 12 (0.76 g, 58% yield) as a pale yellow solid. IR (KBr): 1740 (s), 1690 (s), 1675 (s) $cm^{-1}$. $^1H$ NMR (DMSO-$d_{6, 400}$ MHz): δ 1.20 (t, J=7 Hz, 3H, C$\underline{H}_3$), 2.46–2.52 (m, 1H, ArC$\underline{H}$H), 2.76–3.04 (overlapping m, 4H, Ar CH$\underline{H}$, C$\underline{H}$, C$\underline{HH}CO_2$), 4.08 (q, J=7 Hz, 2H, C$\underline{H}_2$), 6.97 (d, J=8 Hz, 1H, Ar$\underline{H}$), 7.56 (m, 1H, Ar $\underline{H}$), 7.59 (d, J=2H, 1H, Ar$\underline{H}$), 7.65 (t, J=8 Hz, 1H, Ar$\underline{H}$), 7.83 (m, 1H, Ar$\underline{H}$), 7.97 (m, 1H, Ar$\underline{H}$), 8.15 (s, 1H, Ar$\underline{H}$), 10.1 (s, 1H, C$\underline{H}$O), 10.3 (s, 1H, N$\underline{H}$). MS (pos. APCI) m/e (rel. intensity): 338 (M+H, 100). Exact mass calc. for M+H: 338.1387. Found: 338.1383.

Step E Compound 12 (337 mg, 1.0 mmol), compound 8 (247 mg, 1.0 mmol) and 3 Å molecular sieves were combined in methanol (10 mL) at room temperature under nitrogen in a flame-dried flask. Acetic acid (0.12 mL, 2.1 mmol) was added and the mixture was stirred overnight. After 20 hours sodium cyanoborohydride (87 mg, 1.3 mmol) was added and the suspension was stirred for an additional 22 hours, at which time the mixture was filtered (Celite), washed with methanol and concentrated under reduced pressure. The resulting pale yellow foam was treated with $NH_3$-saturated methanol (20 mL) and concentrated. This treatment was repeated to yield a foam. Flash column chromatography on silica gel (30 g) eluting with $NH_3$-saturated $MeOH/CHCl_3$ (gradient elution: 2.5, 5, then 10%) gave the title compound, 13, (180 mg, 32% yield) as a tan foam. IR (KBr): 3315 (broad, m), 1730 (m), 1680 (s) $cm^{-1}$. $^1H$ NMR (DMSO-$d_6$, 400 MHz): δ 1.19 (t, J=7 Hz, 3H, C$\underline{H}_3$), 2.46–2.51 (m, 1H, ArC$\underline{H}$H), 2.60 (overlapping m, 2H, CHC$\underline{HH}$N), 2.74–3.02 (overlapping s, m, 7H, ArCH$\underline{H}$, C$\underline{H}$CONH, C$\underline{HH}CO_2$, $SO_2CH_3$), 3.77 (AB quartet, J=9 Hz, 2H, ArC$\underline{HH}$N), 4.09 (q, J=7 Hz, 2H, OC$\underline{H}_2$), 4.54 (dd, J=5 Hz, 7 Hz, 1H, ArC$\underline{H}$OH), 5.18 (broad s, 1H), 6.79 (d J=8 Hz, 1H, Ar$\underline{H}$), 6.93 (d, J=8 Hz, 1H, Ar$\underline{H}$), 6.97 (m, 1H, Ar$\underline{H}$), 7.16 (d, J=2 Hz, 1H, Ar $\underline{H}$), 7.24 (d, J=7.5 Hz, 1H, Ar$\underline{H}$), 7.34 (t, J=7.5 Hz, 1H, Ar $\underline{H}$), 7.43–7.47 (overlapping s, m, 3H, Ar$\underline{H}$), 7.56 (s, 1H, Ar $\underline{H}$), 9.00 (broad s, 1H, ArN$\underline{H}SO_2$), 10.2 (s, 1H, ArN$\underline{H}$CO). MS (pos. ESI) m/e (rel. intensity): 568 (M+H, 100).

EXAMPLE 3

[7-(3-{[(2R)-2-Hydroxy-2-(4-hydroxy-3-methanesulfonylamino-phenyl)-ethylamino]-methyl}-phenyl)-2-oxo-1,2,3,4-tetrahydro-quinolin-3-yl]-acetic acid methyl ester The title compound was synthesized in the same manner as described in Example 1, using 3-formylphenylboronic acid in place of 4-formylphenylboronic acid in Step E. The title compound (178 mg, 32% yield) was obtained as a tan foam after flash column chromatography. IR (KBr): 3315 (broad, m), 1730 (m), 1680 (s) $cm^{-1}$. $^1H$ NMR (DMSO-$d_6$, 400 MHz): δ 1.19 (t, J=7 Hz, 3H, C$\underline{H}_3$), 2.46–2.51 (m, 1H, ArC$\underline{H}$H), 2.60 (overlapping m, 2H, CHC$\underline{HH}$N), 2.74–3.02 (overlapping s, m, 7H, ArCH$\underline{H}$, C$\underline{H}$CONH, C$\underline{HH}CO_2$, $SO_2CH_3$), 3.77 (AB quartet, J=9 Hz, 2H, ArC$\underline{HH}$N), 4.09 (q, J=7 Hz, 2H, OC $\underline{H}_2$), 4.54 (dd, J=5 Hz, 7 Hz, 1H, ArC$\underline{H}$OH), 5.18 (broad s, 1$\underline{H}$), 6.79 (d, J=8 Hz, 1H, Ar$\underline{H}$), 6.93 (d, J=8 Hz, 1H, Ar$\underline{H}$), 6.97 (m, 1H, Ar$\underline{H}$), 7.16 (d, J=2 Hz, 1H, Ar$\underline{H}$), 7.24 (d, J=7.5 Hz, 1H, Ar$\underline{H}$), 7.34 (t, J=7.5 Hz, 1H, Ar$\underline{H}$), 7.43–7.47 (overlapping s, m, 3H, Ar$\underline{H}$), 7.56 (s, 1H, Ar$\underline{H}$), 9.00 (broad s, 1H, ArN$\underline{H}SO_2$), 10.2 (s, 1H, ArN$\underline{H}$CO). MS (pos. ESI) m/e (rel. intensity): 568 (M+H, 100).

EXAMPLE 4

Ethyl [6-(4-{[(2R)-2-hydroxy-2-{4-hydroxy-3-[(methylsulfonyl)amino]-phenyl}ethyl)amino]methyl}phenyl)-2-oxo-1,2,3,4-tetrahydroquinolin-3-yl] acetate The title compound was synthesized in the same manner as described in Example 2, using 4-formylphenylboronic acid in place of 3-formylphenylboronic acid in Step D. The title compound (173 mg, 31% yield) was obtained as a pale yellow foam after flash column chromatography. IR (KBr): 3275 (broad, m), 1730 (m), 1670 (s) $cm^{-1}$. $^1H$ NMR (DMSO-$d_6$, 400 MHz): δ 2.48–2.53 (m, 1H, ArC$\underline{H}$H), 2.60 (overlapping m, 2H, CHC$\underline{HH}$N), 2.75–2.97 (overlapping s, m, 7H, ArCH$\underline{H}$, C$\underline{H}$CONH, C$\underline{HH}CO_2$, $SO_2CH_3$), 3.61 (s, 3H, OC$\underline{H}_3$), 3.75 (m, 2H, ArC$\underline{HH}$N), 4.55 (m, 1H, ArC $\underline{H}$OH), 5.20 (broad s, 1H), 6.80 (d, J=8 Hz, 1H, Ar$\underline{H}$), 6.98 (m, 1H, Ar$\underline{H}$), 7.11 (d, J=2 Hz, 1H, Ar$\underline{H}$), 7.17–7.24 (overlapping m, 3H, Ar$\underline{H}$), 7.38 (d, J=8 Hz, 2H, Ar$\underline{H}$), 7.49 (d, J=8 Hz, 2H, Ar$\underline{H}$), 9.00 (broad s, 1H, ArN$\underline{H}SO_2$), 10.2 (s, 1H, ArN$\underline{H}$CO). MS (pos. ESI) m/e (rel. intensity): 554 (M+H, 100).

What is claimed is:

1. A compound of formula I having the structure

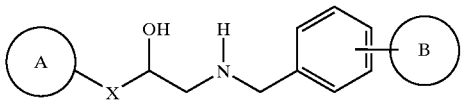

wherein,

a phenyl, optionally substituted with 1–3 Y groups;

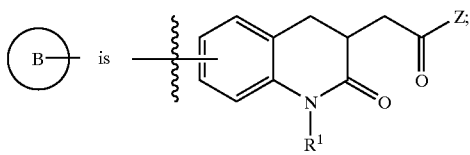

Y is hydroxy, halogen, cyano, —SO$_m$R$^2$, —SO$_n$R$^2$R$^3$, —NHSO$_2$R$^2$, —NR$^2$R$^3$, alkyl of 1–10 carbon atoms, cycloalkyl of 3–8 carbon atoms, alkoxy of 1–10 carbon atoms, arylalkoxy, —COR$^2$, or —CO$_2$R$^2$;

X is a bond;

Z is —OR$^2$ or —NR$^2$R$^3$;

R$^1$ is hydrogen, alkyl of 1–6 carbon atoms, or cycloalkyl of 3–8 carbon atoms;

R$^2$ and R$^3$ are each, independently, hydrogen; alkyl of 1–10 carbon atoms which may be optionally substituted with 1–5 substituents selected from the group consisting of halogen, hydroxy, phenyl optionally substituted with 1–2 W groups, oxo, —CO$_2$R$^4$, —NR$^4$R$^5$, and —NHCOR$^4$; cycloalkyl of 3–8 carbon atoms; arylalkyl having 1–10 carbon atoms in the alkyl moiety; or heterocycle or heterocycle-alkyl, where the alkyl moiety has 1–5 carbon atoms and the heterocycle is:

(a) a 5- or 6-membered heterocyclic ring having 1–4 heteroatoms selected from O, N, and S, optionally substituted with 1–2 Y groups;

(b) a phenyl-fused heterocycle having 1–4 heteroatoms selected from O, N, and S, optionally substituted with 1–2 Y groups; or (c) a phenyl-fused heterocycle having 1–4 heteroatoms selected from O, N, and S, having a second phenyl ring fused to the heterocyclic ring, optionally substituted with 1–2 Y groups;

R$^4$ and R$^5$ are each, independently, hydrogen, alkyl of 1–10 carbon atoms, or cycloalkyl of 3–8 carbon atoms;

W is hydroxy, halogen, alkyl of 1–10 carbon atoms, arylalkoxy having 1–6 carbon atoms in the alkyl moiety, —NHC(O)NHR$^4$, NR$^4$R$^5$, —OR$^4$, —COR$^4$, —CO$_2$R$^4$, —SO$_m$R$^4$, —SO$_n$R$^4$R$^5$;

m=0–2;

n=1–2;

or a pharmaceutically acceptable salt thereof.

2. The compound according to claim 1, wherein

Z is OR$^2$;

R$^1$ is hydrogen;

or a pharmaceutically acceptable salt thereof.

3. The compound of claim 1, which is a) [7-(4-{[(2R)-2-hydroxy-2-(4-hydroxy-3-methanesulfonylamino-phenyl)-ethylamino]-methyl}-phenyl)-2-oxo-1,2,3,4-tetrahydro-quinolin-3-yl]-acetic acid methyl ester;

b) [7-(3-{[(2R)-2-hydroxy-2-(4-hydroxy-3-methanesulfonylamino-phenyl)-ethylamino]-methyl}-phenyl)-2-oxo-1,2,3,4-tetrahydro-quinolin-3-yl]-acetic acid methyl ester;

c) ethyl [6-(4-{[((2R)-2-hydroxy-2-{4-hydroxy-3-[(methylsulfonyl)amino]-phenyl}ethyl)amino]methyl}phenyl)-2-oxo-1,2,3,4-tetrahydroquinolin-3-yl]acetate; or d) ethyl [6-(3-{[((2R)-2-hydroxy-2-{4-hydroxy-3-[(methylsulfonyl)amino]-phenyl}ethyl)amino]methyl}phenyl)-2-oxo-1,2,3,4-tetrahydroquinolin-3-yl]acetate;

or a pharmaceutically acceptable salt thereof.

4. A method of treating metabolic disorders mediated by insulin resistance or hyperglycemia in a mammal in need thereof which comprises providing to said mammal, an effective amount of a compound of formula I having the structure

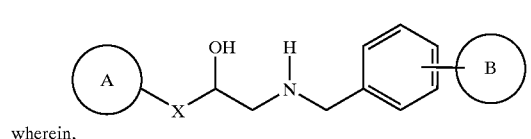

wherein,

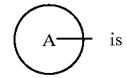

a phenyl, optionally substituted with 1–3 Y groups;

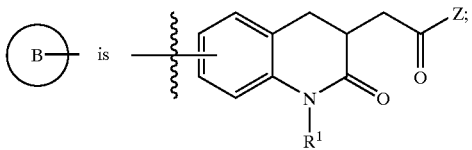

Y is hydroxy, halogen, cyano, —SO$_m$R$^2$, —SO$_n$R$^2$R$^3$, —NHSO$_2$R$^2$, —NR$^2$R$^3$, alkyl of 1–10 carbon atoms, cycloalkyl of 3–8 carbon atoms, alkoxy of 1–10 carbon atoms, arylalkoxy, —COR$^2$, or —CO$_2$R$^2$;

X is a bond;

Z is —OR$^2$ or —NR$^2$R$^3$;

R$^1$ is hydrogen, alkyl of 1–6 carbon atoms, or cycloalkyl of 3–8 carbon atoms;

R$^2$ and R$^3$ are each, independently, hydrogen; alkyl of 1–10 carbon atoms which may be optionally substituted with 1–5 substituents selected from the group consisting of halogen, hydroxy, phenyl optionally substituted with 1–2 W groups, oxo, —CO$_2$R$^4$, —NR$^4$R$^5$, and —NHCOR$^4$; cycloalkyl of 3–8 carbon atoms; arylalkyl having 1–10 carbon atoms in the alkyl moiety; or heterocycle or heterocycle-alkyl, where the alkyl moiety has 1–5 carbon atoms and the heterocycle is:

(a) a 5- or 6-membered heterocyclic ring having 1–4 heteroatoms selected from O, N, and S, optionally substituted with 1–2 Y groups;

(b) a phenyl-fused heterocycle having 1–4 heteroatoms selected from O, N, and S, optionally substituted with 1–2 Y groups; or (c) a phenyl-fused heterocycle having 1–4 heteroatoms selected from O, N, and S, having a second phenyl ring fused to the heterocyclic ring, optionally substituted with 1–2 Y groups;

$R^4$ and $R^5$ are each, independently, hydrogen, alkyl of 1–10 carbon atoms, or cycloalkyl of 3–8 carbon atoms;

W is hydroxy, halogen, alkyl of 1–10 carbon atoms, arylalkoxy having 1–6 carbon atoms in the alkyl moiety, —NHC(O)NHR$^4$, NR$^4$R$^5$, —OR$^4$, —COR$^4$, —CO$_2$R$^4$, —SO$_m$R$^4$, —SO$_n$R$^4$R$^5$;

m=0–2;

n=1–2;

or a pharmaceutically acceptable salt thereof.

5. A method of treating or inhibiting type II diabetes in a mammal in need thereof which comprises providing to said mammal, an effective amount of a compound of Formula I having the structure

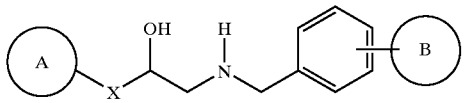

I wherein,

is a phenyl, optionally substituted with 1–3 Y groups;

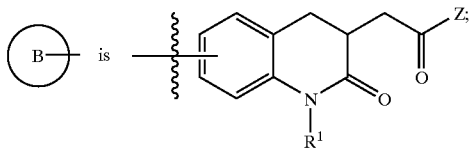

Y is hydroxy, halogen, cyano, —SO$_m$R$^2$, —SO$_n$R$^2$R$^3$, —NHSO$_3$R$^2$, —NR$^2$R$^3$, alkyl of 1–10 carbon atoms, cycloalkyl of 3–8 carbon atoms, alkoxy of 1–10 carbon atoms, arylalkoxy, —COR$^2$, or —CO$_2$R$^2$;

X is a bond;

Z is —OR$^2$ or —NR$^2$R$^3$;

$R^1$ is hydrogen, alkyl of 1–6 carbon atoms, or cycloalkyl of 3–8 carbon atoms;

$R^2$ and $R^3$ are each, independently, hydrogen; alkyl of 1–10 carbon atoms which may be optionally substituted with 1–5 substituents selected from the group consisting of halogen, hydroxy, phenyl optionally substituted with 1–2 W groups, oxo, —CO$_2$R$^4$, —NR$^4$R$^5$, and —NHCOR$^4$; cycloalkyl of 3–8 carbon atoms; arylalkyl having 1–10 carbon atoms in the alkyl moiety; or heterocycle or heterocycle-alkyl, where the alkyl moiety has 1–5 carbon atoms and the heterocycle is:

(a) a 5- or 6-membered heterocyclic ring having 1–4 heteroatoms selected from O, N, and S, optionally substituted with 1–2 Y groups;

(b) a phenyl-fused heterocycle having 1–4 heteroatoms selected from O, N, and S, optionally substituted with 1–2 Y groups; or (c) a phenyl-fused heterocycle having 1–4 heteroatoms selected from O, N, and S, having a second phenyl ring fused to the heterocyclic ring, optionally substituted with 1–2 Y groups;

$R^4$ and $R^5$ are each, independently, hydrogen, alkyl of 1–10 carbon atoms, or cycloalkyl of 3–8 carbon atoms;

W is hydroxy, halogen, alkyl of 1–10 carbon atoms, arylalkoxy having 1–6 carbon atoms in the alkyl moiety, —NHC(O)NHR$^4$, NR$^4$R$^5$, —OR$^4$, —COR$^4$, —CO$_2$R$^4$, —SO$_m$R$^4$, —SO$_n$R$^4$R$^5$;

m=0–2;

n=1–2;

or a pharmaceutically acceptable salt thereof.

6. A method of modulating glucose levels in a mammal in need thereof which comprises providing to said mammal, an effective amount of a compound of formula I having the structure

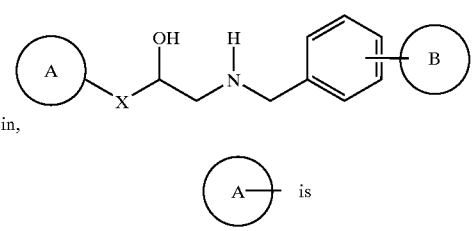

I wherein,

A⟩— is a phenyl, optionally substituted with 1–3 Y groups;

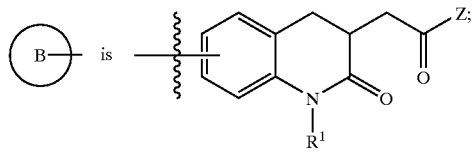

Y is hydroxy, halogen, cyano, —SO$_m$R$^2$, —SO$_n$R$^2$R$^3$, —NHSO$_2$R$^2$, —NR$^2$R$^3$, alkyl of 1–10 carbon atoms, cycloalkyl of 3–8 carbon atoms, alkoxy of 1–10 carbon atoms, arylalkoxy, —COR$^2$, or —CO$_2$R$^2$;

X is a bond;

Z is —OR$^2$ or —NR$^2$R$^3$;

$R^1$ is hydrogen, alkyl of 1–6 carbon atoms, or cycloalkyl of 3–8 carbon atoms; $R^2$ and $R^3$ are each, independently, hydrogen; alkyl of 1–10 carbon atoms which may be optionally substituted with 1–5 substituents selected from the group consisting of halogen, hydroxy, phenyl optionally substituted with 1–2 W groups, oxo, —CO$_2$R$^4$, —NR$^4$R$^5$, and —NHCOR$^4$; cycloalkyl of 3–8 carbon atoms; arylalkyl having 1–10 carbon atoms in the alkyl moiety; or heterocycle or heterocycle-alkyl, where the alkyl moiety has 1–5 carbon atoms and the heterocycle is:

(a) a 5- or 6-membered heterocyclic ring having 1–4 heteroatoms selected from O, N, and S, optionally substituted with 1–2 Y groups;

(b) a phenyl-fused heterocycle having 1–4 heteroatoms selected from O, N, and S, optionally substituted with 1–2 Y groups; or (c) a phenyl-fused heterocycle having 1–4 heteroatoms selected from O, N, and S, having a second phenyl ring fused to the heterocyclic ring, optionally substituted with 1–2 Y groups;

$R^4$ and $R^5$ are each, independently, hydrogen, alkyl of 1–10 carbon atoms, or cycloalkyl of 3–8 carbon atoms;

W is hydroxy, halogen, alkyl of 1–10 carbon atoms, arylalkoxy having 1–6 carbon atoms in the alkyl moiety, —NHC(O)NHR$^4$, NR$^4$R$^5$, —OR$^4$, —COR$^4$, CO$_2$R$^4$, —SO$_m$R$^4$, —SO$_n$R$^4$R$^5$;

m=0–2;
n=1–2;
or a pharmaceutically acceptable salt thereof.

7. A pharmaceutical composition which comprises a compound of formula I having the structure

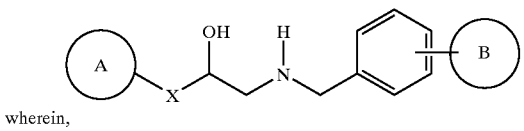

I wherein,

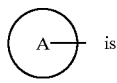

a phenyl, optionally substituted with 1–3 Y groups;

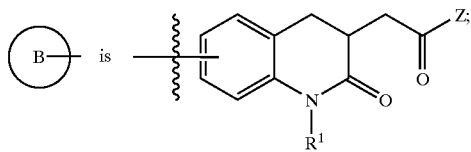

Y is hydroxy, halogen, cyano, —$SO_mR^2$, —$SO_nR^2R^3$, —$NHSO_2R^2$, —$NR^2R^3$, alkyl of 1–10 carbon atoms, cycloalkyl of 3–8 carbon atoms, alkoxy of 1–10 carbon atoms, arylalkoxy, —$COR^2$, or —$CO_2R^2$;

X is a bond;

Z is —$OR^2$ or —$NR^2R^3$;

$R^1$ is hydrogen, alkyl of 1–6 carbon atoms, or cycloalkyl of 3–8 carbon atoms;

$R^2$ and $R^3$ are each, independently, hydrogen; alkyl of 1–10 carbon atoms which may be optionally substituted with 1–5 substituents selected from the group consisting of halogen, hydroxy, phenyl optionally substituted with 1–2 W groups, oxo, —$CO_2R^4$, —$NR^4R^5$, and —$NHCOR^4$; cycloalkyl of 3–8 carbon atoms; arylalkyl having 1–10 carbon atoms in the alkyl moiety; or heterocycle or heterocycle-alkyl, where the alkyl moiety has 1–5 carbon atoms and the heterocycle is:

(a) a 5- or 6-membered heterocyclic ring having 1–4 heteroatoms selected from O, N, and S, optionally substituted with 1–2 Y groups;

(b) a phenyl-fused heterocycle having 1–4 heteroatoms selected from O, N, and S, optionally substituted with 1–2 Y groups; or (c) a phenyl-fused heterocycle having 1–4 heteroatoms selected from O, N, and S, having a second phenyl ring fused to the heterocyclic ring, optionally substituted with 1–2 Y groups;

$R^4$ and $R^5$ are each, independently, hydrogen, alkyl of 1–10 carbon atoms, or cycloalkyl of 3–8 carbon atoms;

W is hydroxy, halogen, alkyl of 1–10 carbon atoms, arylalkoxy having 1–6 carbon atoms in the alkyl moiety, —$NHC(O)NHR^4$, $NR^4R^5$, —$OR^4$, —$COR^4$, —$CO_2R^4$, —$SO_mR^4$, —$SO_nR^4R^5$;

m=1–2;

n=1–2;

or a pharmaceutically acceptable salt thereof.

* * * * *